(12) United States Patent
Snyder et al.

(10) Patent No.: US 6,287,328 B1
(45) Date of Patent: Sep. 11, 2001

(54) MULTIVARIABLE ARTIFACT ASSESSMENT (75) Inventors: David E Snyder, Bainbridge Island; Thomas D Lyster, Bothell, both of WA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/288,584

(22) Filed: Apr. 8, 1999

(51) Int. Cl.$^7$ .......................................................... A61B 5/04
(52) U.S. Cl. ............................................. 607/509; 607/513
(58) Field of Search ....................................... 607/509, 513

(56) References Cited

U.S. PATENT DOCUMENTS

| | | |
|---|---|---|
| 3,559,193 | 1/1971 | Savaglio et al. . |
| 3,580,243 | 5/1971 | Johnson . |
| 3,602,215 | 8/1971 | Parnell . |
| 3,868,947 | 3/1975 | Holsinger . |
| 3,905,364 | 9/1975 | Cudahy et al. . |
| 4,112,930 | 9/1978 | Feldman et al. . |
| 4,194,511 | 3/1980 | Feldman . |
| 4,200,109 | 4/1980 | McMorrow, Jr. . |
| 4,243,044 | 1/1981 | Blancke . |
| 4,291,699 | 9/1981 | Gedes et al. . |
| 4,533,876 | 8/1985 | Haque et al. . |
| 4,598,281 | 7/1986 | Maas . |
| 4,610,254 | 9/1986 | Morgan et al. . |
| 4,619,265 | 10/1986 | Morgan et al. . |
| 4,746,910 | * 5/1988 | Pfister et al. . |
| 4,785,812 | 11/1988 | Pihl et al. . |
| 4,796,638 | 1/1989 | Sasaki . |
| 4,802,486 | 2/1989 | Goodman et al. . |
| 4,896,120 | 1/1990 | Kamil . |

(List continued on next page.)

FOREIGN PATENT DOCUMENTS

| | | |
|---|---|---|
| WO 83/10374 | 4/1983 | (WO) . |
| WO 96/27326 | 9/1996 | (WO) ........................... A61B/5/0424 |

OTHER PUBLICATIONS

"A Method for the Measurement of the Properties of Individual Electrode—Skin Interfaces And The Implicatinons of the Electrode Properties for Preamplifier Design", Gaimbergen et al, Proceedings of the Annual Intel. Conference of IEEE Engineering in Medicine & Biology Society, vol. 14, Part 6, Nov. 1, 1992, pp. 2382–2383.

*Primary Examiner*—Carl H. Layno (57) ABSTRACT

An apparatus detects corruption of an event signal by two or more non-event artifacts by using multivariable artifact assessment. The apparatus comprises: 1) a sensor for providing an input signal comprising an event signal coexisting with two or more non-event signals, 2) a measurement system including a receiver for receiving the input signal from the sensor and separating the received input signal into its constituent parts, 3) detectors for detecting both the event signal and non-event signals from the received input signal, and 4) an inference processor for analyzing the correlation signals to produce an indication of signal corruption. In a second embodiment, the apparatus comprises: 1) a plurality of sensors for providing additional non-event input signals, 2) a corresponding measurement system having a plurality of receivers for receiving the additional input signals, 3) detectors for detecting the non-event signals from the received additional input signals, 4) correlators for comparing the detected event signal with each of the detected non-event signals to produce respective correlation signals, and 5) an inference processor for analyzing the correlation signals to produce an indication of signal corruption. The apparatus may be a patient monitoring system or a defibrillator. Methods of operating the apparatus are also described.

24 Claims, 7 Drawing Sheets

U.S. PATENT DOCUMENTS

| | | |
|---|---|---|
| 4,917,099 | 4/1990 | Stice . |
| 4,919,144 | 4/1990 | Vandehey . |
| 4,919,145 | 4/1990 | Marriott . |
| 4,993,423 | 2/1991 | Stice . |
| 5,002,063 | 3/1991 | Haner . |
| 5,020,541 | 6/1991 | Marriott . |
| 5,025,808 | 6/1991 | Hafner . |
| 5,107,849 | 4/1992 | Bellin et al. . |
| 5,184,615 | 2/1993 | Nappholz et al. . |
| 5,231,990 | 8/1993 | Gauglitz . |
| 5,247,939 | 9/1993 | Sjoquist et al. . |
| 5,376,104 | 12/1994 | Sakai et al. . |
| 5,392,784 | 2/1995 | Gudaitis . |
| 5,427,111 | 6/1995 | Traub et al. . |
| 5,474,574 | 12/1995 | Payne et al. . |
| 5,490,505 | 2/1996 | Diab et al. . |
| 5,503,160 | 4/1996 | Pering et al. . |
| 5,558,098 | 9/1996 | Fain . |
| 5,632,280 | 5/1997 | Leyde et al. . |
| 5,647,379 * | 7/1997 | Meltzer . |
| 5,650,750 | 7/1997 | Leyde et al. . |
| 5,902,249 | 5/1999 | Lyster . |

* cited by examiner

MULTIVARIABLE ARTIFACT ASSESSMENT

FIELD OF THE INVENTION

The present invention relates in general to an artifact assessment method and an apparatus for detecting corruption of signals by artifact using multivariable artifact analysis.

BACKGROUND OF THE INVENTION

One common problem associated with the use of measurement instruments is erroneous measurements that result from the introduction of an artifact signal into the event signal of interest. Typically a measurement instrument detects a single measured signal comprised of the event signal of interest along with some level of artifact related to one or more non-event signals. The resulting measured signal can become significantly corrupted such that it should not be relied upon as an accurate representation of the event signal. Artifact which corrupts the event signal can result from mechanical disturbances of sensors, electromagnetic interference, etc. As will be appreciated by those of skill in the art, the nature of the artifact signals will vary depending on the nature of the measuring instrument and the environmental conditions under which the measurements are taken.

One area in which the presence of artifact signals presents a potentially life-threatening problem is in the area of medical diagnostics and instrumentation. The appearance of an undetected non-event signal in a patient monitoring device could result in a clinician making an incorrect decision with respect to a patient's treatment, or, for devices that use algorithms to make decisions, could result in the device itself making an incorrect assessment of the patient's condition.

In the area of cardiac monitoring, a common-mode signal is just one type of non-event signal that can cause corruption of the measurement of the event signal of interest. Cardiac monitors measure a differential-mode signal between two or more electrodes. Typical examples of devices that measure differential-mode signal include an electrocardiograph ("ECG") monitoring system, and defibrillator systems. These systems use a plurality of electrodes to measure a differential signal generated by the heart. In operation, the plurality of electrodes are placed advantageously on the patient. As is well known by clinicians, these differential-mode signals are of interest because they give an indication of the state of the patient's heart (e.g. normal beat pattern versus ventricular fibrillation ("VF")).

As is well known in the art, common-mode signals (i.e. signals that appear simultaneously upon both inputs of a differential amplifier with essentially equal magnitude, frequency, and phase) can become superimposed upon the differential-mode signals of interest (e.g., the ECG signal generated by the heart) and are sometimes converted by the system into differential-mode signals themselves. As discussed in U.S. Pat. No. 5,632,280 Leyde et al., this conversion may lead to the ultimate corruption of the differential-mode signals of interest and, in the case of a defibrillator, may lead to a potentially harmful misdiagnosis of the patient's true heart condition.

In addition to common-mode signals, the event signal can be corrupted by signals resulting from mechanical movement of the electrodes. In the cardiac monitoring setting, such mechanical movement could be, for example, the result of CPR being performed on the patient. The mechanical movement of the patient's chest is transmitted to the electrodes which then superimposes that artifact signal over the event signal to produce a corrupted signal which is measured by the device.

Because the possibility of misdiagnosis has potentially serious consequences, several attempts have been made to minimize the effect of artifact in an event signal. These efforts have, by and large, been concerned with either the elimination or suppression of the artifact signals. By reducing artifact signals, the contribution of their effects on the composite signal measured by the device is similarly reduced.

In a specific example, the reduction of common-mode signals has taken several forms. The first common method is capacitance reduction. As is well known in the art, common-mode voltages induce common-mode currents inversely proportional to the total impedance around the loop between the patient, the system, and the common-mode voltage sources. To reduce common-mode currents, this impedance is made as large as possible by minimizing the capacitance between the system and its cables to the outside world.

Nevertheless, capacitance minimization has its limitations. Circuits and cabling occupy certain minimum physical areas, and capacitance can only be reduced by increasing the distance from these circuits to outside references. Outside references may be the earth, or objects outside the instrument, or may even be other parts of the same instrument that have different potential references.

For example, many medical instruments maintain "isolated" circuits connected to patients for safety reasons. These circuits maintain a local potential reference not electrically connected to other references in order to reduce accidental electrical injuries. In these cases, reducing the capacitance to such "isolated" circuits means that spacing must be maximized within the instruments between the isolated circuits and other portions of the instrument, the instrument enclosure, or objects in the outside world. However, it is also important to limit the physical size of instrumentation, so that increasing available spacing has practical limitations as a means of limiting common-mode currents.

A second major effort to reduce common-mode currents is shielding. In this case, the shields are equipotential surfaces such as metal enclosures, that are used to block the entry of electromagnetic fields into instruments and cabling. Such fields may originate, for example, from power lines, radio transmitters, or nearby moving charged objects and may induce common-mode currents in circuits they encounter.

However, instrument shielding does not include the patient—a major source of common-mode coupling. The shielding of the instrumentation system thus does nothing to prevent the presentation of large common-mode sources at electrode connections, after which common-to-differential mode conversion proceeds without inhibition. Shielding can, in fact, make matters worse by increasing capacitance between the instrument ground and earth ground, thus facilitating common-mode current flow.

Closely tailored to the inadequacies of shielding, a third common-mode signal reduction method is the use of extra electrodes to shunt currents around the leads in an effort to eliminate the common-mode current. In some systems, a third electrode is attached to the patient and connected to the instrument potential reference to shunt common-mode currents around the differential electrode leads. This results in a reduction—but not elimination—of common-mode currents in the differential input leads. Also, the addition of a third electrode adds complication to circuitry that minimally requires only two patient electrodes.

A fourth method for reducing the effects of common-mode signals is filtering. Some common-mode signals, especially those at low frequencies (e.g. below 1 Hz) or at power line frequencies, lie outside the normal pass-band desired for ECG signals (usually between 0.5–40 Hz) and thus the composite signal can be improved by pass-band filtering. Nevertheless, much of the energy in both common-mode artifacts and ECG signals occupy the same part of the spectrum, which limits the effectiveness of filtering. Many artifacts encountered in patient treatment fall into the normal ECG pass-band and have time characteristics that mimic ECG signals.

As mentioned above, none of these methods for dealing with the presence of common-mode signal completely eliminate the effects of converted common-to-differential mode signal. Thus, the potential for misdiagnosis is still a very real and serious possibility—even after these above suppression techniques have been applied.

Another approach to minimizing the effect of artifact is to detect common-mode artifact signals within a potentially corrupted ECG signal. U.S. Pat. No. 5,650,750 to Leyde et al. (incorporated herein by reference) discloses an apparatus and method for detecting the presence of differential-mode signals where the signals might be corrupted by common-mode signals. The apparatus provides a low common-mode signal impedance with a relatively high differential-mode impedance. This apparatus prevents small common-mode currents from being translated into large common-mode voltages which might then be undesirably passed through by an amplifier block. As will be appreciated by those of skill in the art, the passage of such common-mode voltages is undesirable because the voltages are subsequently superimposed upon the differential-mode voltages, which may lead to false-positive or false-negative diagnosis of a patient's need for defibrillation. However, the Leyde apparatus is not necessarily capable of detecting artifacts caused by motion. Additionally, other types of artifacts might also be incapable of detection with such apparatus and method.

In another example, U.S. Pat. No. 5,247,939 to Sjoquist, et al. (the specification of which is incorporated herein) describes an approach for detecting motion that could give rise to artifact signal in an ECG signal. Sjoquist discloses a defibrillator/monitor employing a motion detection circuit with control and processing circuits that detect motion at a patient-electrode interface. More specifically, patient electrodes are used to detect an ECG signal from a patient, and to further detect motion-induced impedance variations at the different electrode/patient interfaces which might cause the ECG signals from the patient to be misinterpreted by the defibrillator/monitor. Accordingly, the defibrillator/monitor is able to detect motion and inhibit operation until motion is no longer present. Hence, when the detected impedance variation exceeds a specific value, the ECG signal is determined to be corrupted such that a defibrillating shock is prevented. However, significant motion related artifact may exist in the ECG without sufficient impedance variation to be detected. Also, this implementation will not detect other types of artifact that may be present. For example, common-mode current induced artifact will not be detected since it does not necessarily result in an impedance variation. Therefore, a shock might be inappropriately delivered or withheld.

Furthermore, it is possible to have motion, which would be detected, without producing an artifact that significantly alters the ECG signal. Because there is no process of correlating the motion detection signal with the potentially corrupted ECG signal, the device cannot distinguish between motion that effects the ECG signal and motion that does not effect the signal; resulting in a situation where treatment may be inappropriately withheld. For example, a patient who is convulsing due to cardiac arrest is likely to have some motion due to significant muscle contraction (e.g., agonal gasping). This movement may not produce a motion that generates a discernable artifact within the ECG signal. Accordingly, for such cases, it is desirable to more precisely detect the presence of artifact and its effect on the event signal of interest so that more effective patient treatment is given.

Thus, what is needed is an improved method for detecting the presence and significance of artifact signals which may corrupt an event signal. More specifically what is needed is an improved method for detecting the presence and significance of artifact from multiple potential sources within a cardiac event signal or ECG signal.

SUMMARY OF THE INVENTION

The present invention is a novel method and apparatus for analyzing a potentially corrupted event signal, and one or more non-event signals, in order to determine whether the presence of artifact in the event signal precludes an accurate assessment of the event signal of interest.

In one embodiment, an apparatus is provided for detecting corruption of an event signal with artifact in an environment where the potentially corrupted event signal coexists with two or more non-event signals which may be related to the artifact. The apparatus comprises, a sensor for providing an input signal, wherein the input signal comprises an event signal coexisting with two or more non-event signals; a measurement system for receiving the input signal from the sensor and separating the received input signal into its constituent parts, wherein the measurement system comprises a receiver for receiving the input signal, a detector for detecting the event signal from the received input signal, and detectors for detecting the non-event signals from the received input signal; correlators for comparing the detected event signal with each of the detected non-event signals to produce respective correlation signals; and an inference processor for analyzing the correlation signals to produce an indication of signal corruption.

Several specific implementations of the first embodiment are contemplated. For example, in one specific embodiment, the apparatus is a patient monitoring system capable of monitoring a plurality of patient parameters. Patient parameters include, but are not limited to, ECG, EEG, pulse, temperature, or any other biological function or activity. These patient parameters would be the event signals of interest. In a more specific implementation, the apparatus is a defibrillator capable of measuring an ECG. In that instance, the ECG would be the event signal of interest.

The inference processor of the apparatus may analyze the correlation signals to determine if the event signal is corrupted. Alternatively, the inference processor may analyze the correlation signals to determine a degree of corruption of the event signal. Inference processors are typically selected from the group consisting of: peak detectors, polynomial regressions, fuzzy set operations, neural networks, probability estimators, and statistical classifiers.

The coexistent signals, which are part of the input signal, are typically selected from the group consisting of: differential voltage, impedance, and common-mode current. A plurality of signal processors for processing the event and non-event signals prior to correlation may be provided. These signal processors would typically be selected from the group consisting of linear and non-linear transforms. Alternatively, the signal processors could be selected from the group consisting of: filters, Fourier transforms, wavelet transforms, and joint time-frequency spectrograms In an alternative embodiment of the invention, the apparatus comprises: a sensor for providing a first input signal, wherein the first input signal comprises the event signal; at least one additional sensor for providing at least one additional input signal, wherein the additional input signal comprises non-event signals; a measurement system for receiving the input signals from the sensors and detecting the event and non-event signals, wherein the measurement system comprises a receiver for receiving the first input signal, a detector for detecting an event signal from the received first input signal, receivers for receiving the additional input signals, and detectors for detecting the non-event signals from the received additional input signals; correlators for comparing the detected event signal with each of the detected non-event signals to produce respective correlation signals; and an inference processor for analyzing the correlation signals to produce an indication of signal corruption.

As with the above embodiment, several specific implementations of the second embodiment are contemplated. For example, in one specific embodiment, the apparatus is a patient monitoring system capable of monitoring a plurality of patient parameters. Patient parameters include, but are not limited to, ECG, EEG, pulse, temperature, or any other biological activity. These patient parameters would be the event signals of interest. In a more specific implementation, the apparatus is a defibrillator capable of measuring an ECG. In that instance, the ECG would be the event signal of interest.

This embodiment may alternatively be provided with a plurality of additional sensors for providing a plurality of non-event input signals.

In either case, the inference processor may analyze the correlation signals to determine if the event signal is corrupted. Alternatively, the inference processor may analyze the correlation signals to determine a degree of corruption of the event signal. Such inference processors are typically selected from the group consisting of: peak detectors, polynomial regressions, fuzzy set operations, neural networks, probability estimators, and statistical classifiers. The apparatus may also have a plurality of signal processors for processing the event and non-event signals prior to correlation. These signal processors are typically selected from the group consisting of linear and non-linear transforms. More specifically, the signal processors are selected from the group consisting of: filters, Fourier transforms, wavelet transforms, and joint time-frequency spectrograms.

Alternatively, in either case, in an environment where the input signals may have additional coexistent non-event signals, the measurement system may additionally separate the input signals from the sensors into their constituent parts providing additional non-event signals.

Several methods may be employed to operate the invention, or any of the specific embodiments, described above. In a first method, the integrity of the event signal is determined using an apparatus for detecting corruption of an event signal with artifact in an environment where the potentially corrupted event signal coexists with two or more non-event signals which may be related to the artifact. The integrity is determined by: sensing an input signal; detecting the input signal by a measurement system; separating the input signal into constituent parts; correlating the resulting constituent parts to produce a correlated signal; providing the correlated signal to an inference processor; and then determining whether the event signal can be used with confidence. The separating and correlating steps are repeated a plurality of times so that more than one correlated signal is provided to the inference processor.

The inference processor may also compare the correlated signal to a threshold value. Alternatively, the inference processor may analyze the correlated signal data to determine the probability of artifact. It is also contemplated that the detecting step may be repeated a plurality of times to provide more than one input to the device.

In an alternative method of the invention, the method is performed by: sensing a plurality of input signals with a plurality of sensors; detecting the input signals from the sensors by a measurement system; separating at least one input signal into constituent parts; correlating the resulting constituent parts to produce a correlated signal; providing the correlated signal along with at least one additional input signal to an inference processor; and then determining whether the event signal can be used with confidence.

Again, the inference processor may compare the correlated signal to a threshold value. Alternatively, the inference processor may analyze the correlated signal data to determine the probability of artifact.

For a full understanding of the present invention, reference should be made to the detailed description of the preferred embodiments and to the accompanying drawings. However, other features and advantages of the present invention will be apparent to persons of skill in the art from the following description of the preferred embodiments, and from the claims.

BRIEF DESCRIPTION OF THE DRAWINGS

FIGS. 4A and 4B show two variations for treatment of the output from FIGS. 3A–3C. In FIG. 4A, the output is compared to an inference threshold for a YES/NO determination on whether to accept or reject the cardiac event signal for further assessment.

DETAILED DESCRIPTION OF THE INVENTION

Figure 1:
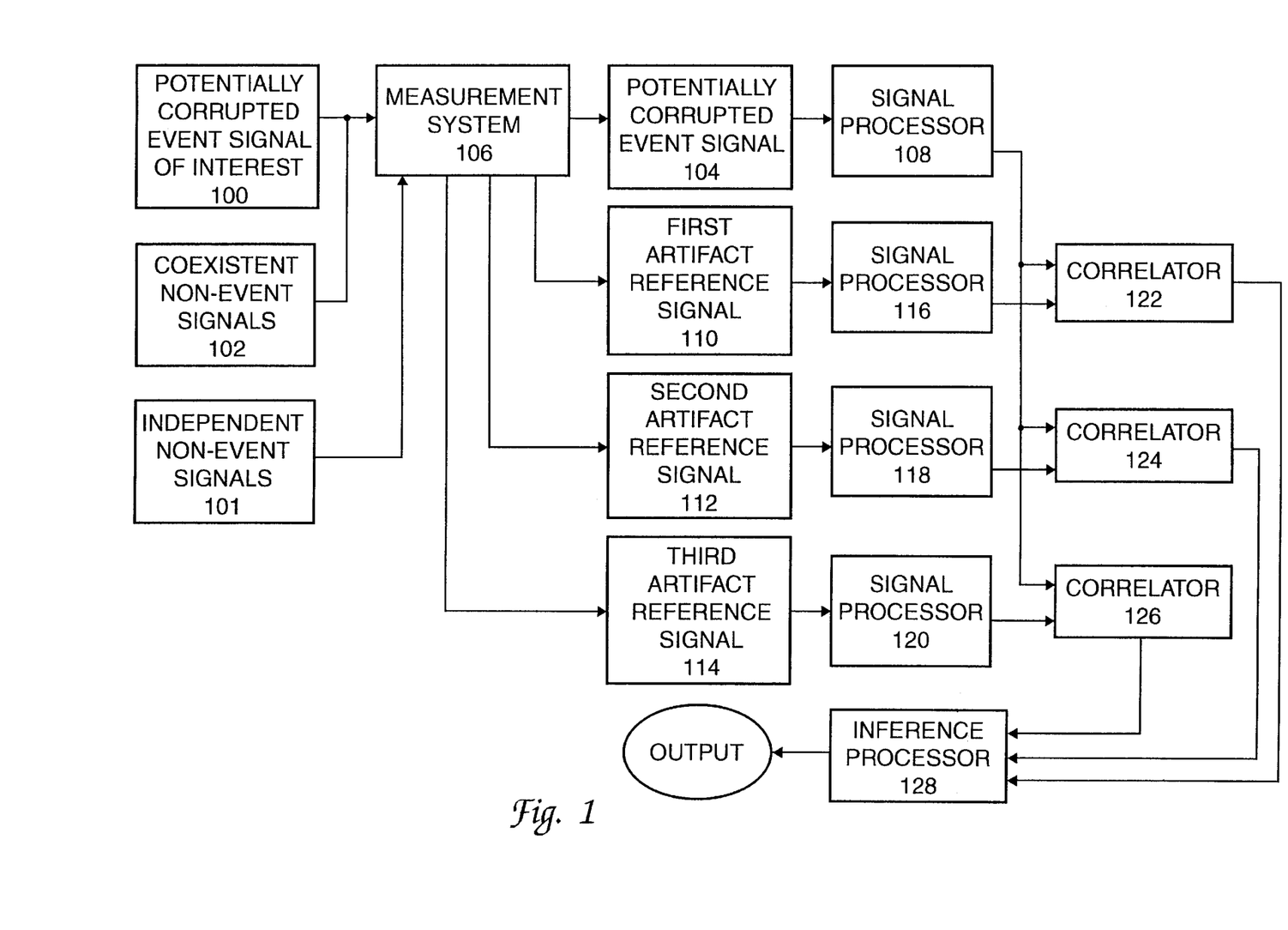
FIG. 1 is a block diagram showing a general embodiment of the invention wherein an event signal of interest combined with artifact signals, are acquired by a measurement system. The signals are then processed and correlated prior to being analyzed by an inference processor. The inference processor then produces an output indicating a degree of artifact corruption.

FIG. 1 is a high-level block diagram demonstrating how a device operating according to this method would receive a potentially corrupted event signal with coexistent non-event signals, as well as independent non-event signals, and separate the coexistent signals into constituent parts. Thereafter, the potentially corrupted event signal is compared to the non-event signals (also known as artifact reference signals) to determine whether the potentially corrupted event signal was significantly corrupted with artifact. As shown in FIG. 1, the potentially corrupted event signal of interest 100 coexists with one or more non-event signals 102 which may be functionally related to the artifact. Measurement system 106 measures the coexistent signals 100, 102 as well as independent non-event signals 101, which may be functionally related to the artifact. These non-event signals may be a component of the composite input signal, or may be derived from separate sensors. The measurement system 106 additionally separates the coexistent signals and then provides the potentially corrupted event signal 104, and individual non-event signals 110, 112, 114 which serve as artifact references.

These event and non-event signals are processed through signal processors 108, 116, 118, 120. As will be appreciated by those of skill in the art, an appropriate signal processing step includes, for example, band-pass filters, Fourier transforms, wavelet transforms, and joint time-frequency spectrograms.

Combinations of these processed signals are then transmitted to correlators 122, 124, 126, which perform correlations between the processed event signal and each of the processed non-event signals. The results of each of the correlations are provided to the inference processor 128 for evaluation to provide and indication of the degree of corruption of the event signal 104.

Further, the method of correlating the data can be any correlation method known in the art. For example, correlation methods include specific and general cross-correlation techniques, which includes known mathematical functions as well as any process that effectively correlates the data. Specific implementations include, but are not limited to, finite sampled or continuous estimates of cross-covariance and cross-correlation, both biased and unbiased. Alternatively, correlation may perform similarity comparisons between any of multiple signals.

Finally, an inference processor is any expert system that contains a problem solving algorithm that can review the data received from the correlators in order to make a more refined estimate of the degree of artifact present in the event signal. Alternative outputs from the inference processor include, but are not limited to, an indication of the probability of artifact, an estimate of the ratio of signal level to artifact level, a fuzzy set membership function, or a Boolean indicator of the presence of artifact.

As will be appreciated by those of skill in the art, this artifact detection technique can be used to detect artifact from any measured input signal source. For example, equipment that is used to measure ocean temperature, seismic activity, etc. can be set-up so that additional input signals are provided for signal processing and correlation with the signal of interest in order to determine whether the signal of interest has been corrupted with artifact. In addition this technique can be applied to systems which measure multiple event signals, wherein each event signal would employ this artifact detection method. For purposes of illustration, the artifact detection technique is described below in conjunction with cardiac monitoring equipment, and specifically defibrillators.

Figure 2:
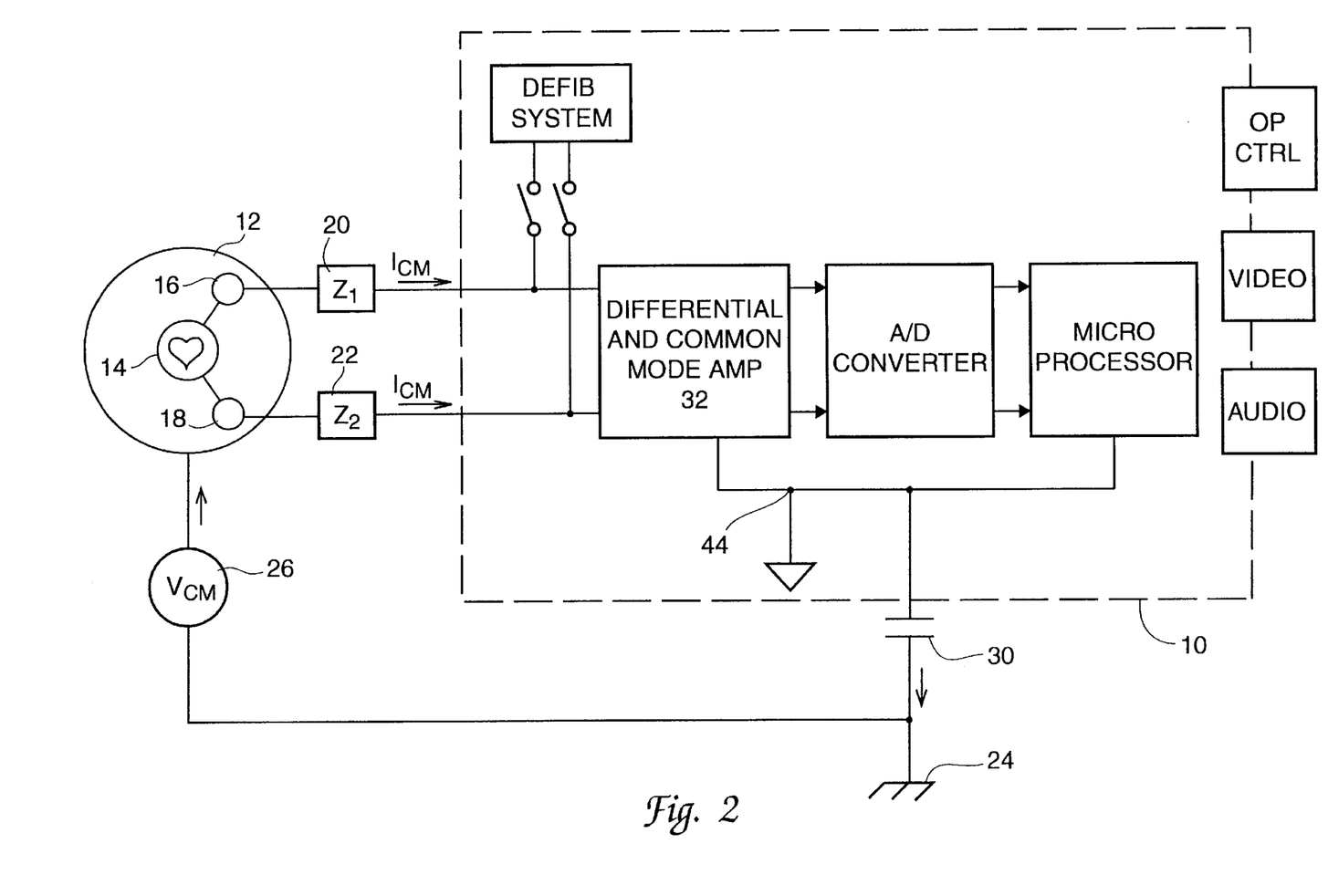
FIG. 2 is a simplified schematic diagram of a defibrillator with an input amplifier that detects event and non-event signals by separating the differential-mode and common-mode components of the input signal for use by subsequent portions of the artifact detector.

FIG. 2 is a block diagram demonstrating one aspect of a defibrillator system 10 made in accordance with this invention. Defibrillator 10 is connected to a patient 12 by electrodes 16 and 18 advantageously placed proximate to heart 14 which outputs a differential mode signal, $V_{ECG}$. Electrodes 16 and 18 have associated impedances 20 and 22 respectively and are schematically represented by $Z_1$ and $Z_2$. Electrodes 16 and 18 may also further be comprised of multiple conductive elements which are in a relatively annular relationship towards each other. Such electrodes are described in more detail in co-pending application for "Electrode System for Improved Detection of Pad Contact and Artifact Detection" by David E. Snyder filed concurrently herewith and incorporated herein.

As described above, common-mode signals are a common source of artifact in the cardiac monitoring environment. As is well known in the art, common-mode signals may arise through many sources. One such source 26 ("$V_{CM}$") induces a common-mode current 28 ("$I_{CM}(t)$") that follows a path in FIG. 2 from earth ground 24, through patient 12 and electrodes 16 and 18, through defibrillator 10, and back to earth ground 24 via a stray capacitance 30 ("$C_{INS}$"). Common-mode currents, such as $I_{CM}(t)$, coexist with (are superimposed with) differential mode signals (which, in this case, are the event signals of interest) generated by the heart.

These coexistent common-mode signals are input into defibrillator 10 along with the differential mode signals via electrodes 16 and 18 into differential and common-mode amplifier block 32. Imbalanced electrode impedances 20, 22 will convert common mode current $I_{CM}$ into a differential voltage which is combined with the cardiac event signal 14. Additionally, in a typical amplifier, some amount of common-mode signal is converted into differential mode signal and passed along in the output as differential mode signals. These converted common-mode signal sometimes dominates the differential output of the amplifier and the potential for misdiagnosis of the differential mode signal of interest exists. This input signal (containing both common-mode and differential mode signals) is then processed and provided to a correlator to determine whether a significant amount of artifact is present in the signal. The processing can be performed as described in more detail in co-pending application 08/755,273, the specification of which is incorporated herein.

Figure 3A:
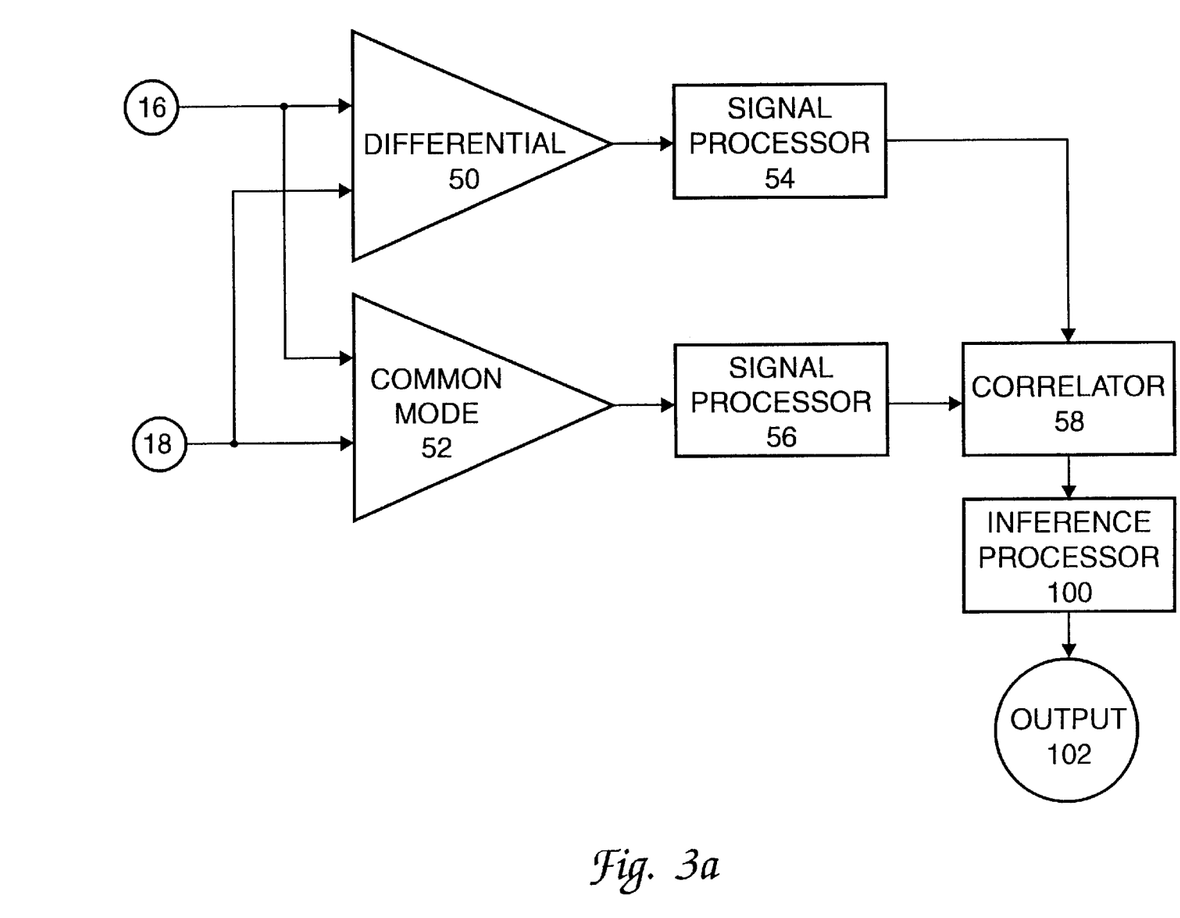
FIG. 3A is a simplified schematic diagram showing connection of an input signal to the differential mode amplifier and common-mode amplifier. The amplifiers then provide the signal to the signal processors which process the signal and provides the processed signals to the correlator which is in turn provided to the inference processor.

FIG. 3A is a simplified circuit depicting the signal processing method for detecting common-mode current for use as a non-event signal (artifact reference signal), which is one aspect of the invention. The input signal is received across the electrodes 16, 18 and transmitted to differential-mode amplifier 50, and common-mode amplifier 52 which amplify the signal prior to transmitting the signal to the signals processors. The resulting signals, representing the potentially corrupted event signal, and the artifact reference signal respectively, are then transmitted to their respective signal processors 54, 56 which process the signals to emphasize particular features. The resulting processed signals are then transmitted to a correlator 58 which correlates the signals.

The results of the correlator is then provided to an inference processor 100 which evaluates the results of the correlator and provides an output 102. Treatment of the output 102 will be discussed below in conjunction with FIG. 4.

Figure 3B:
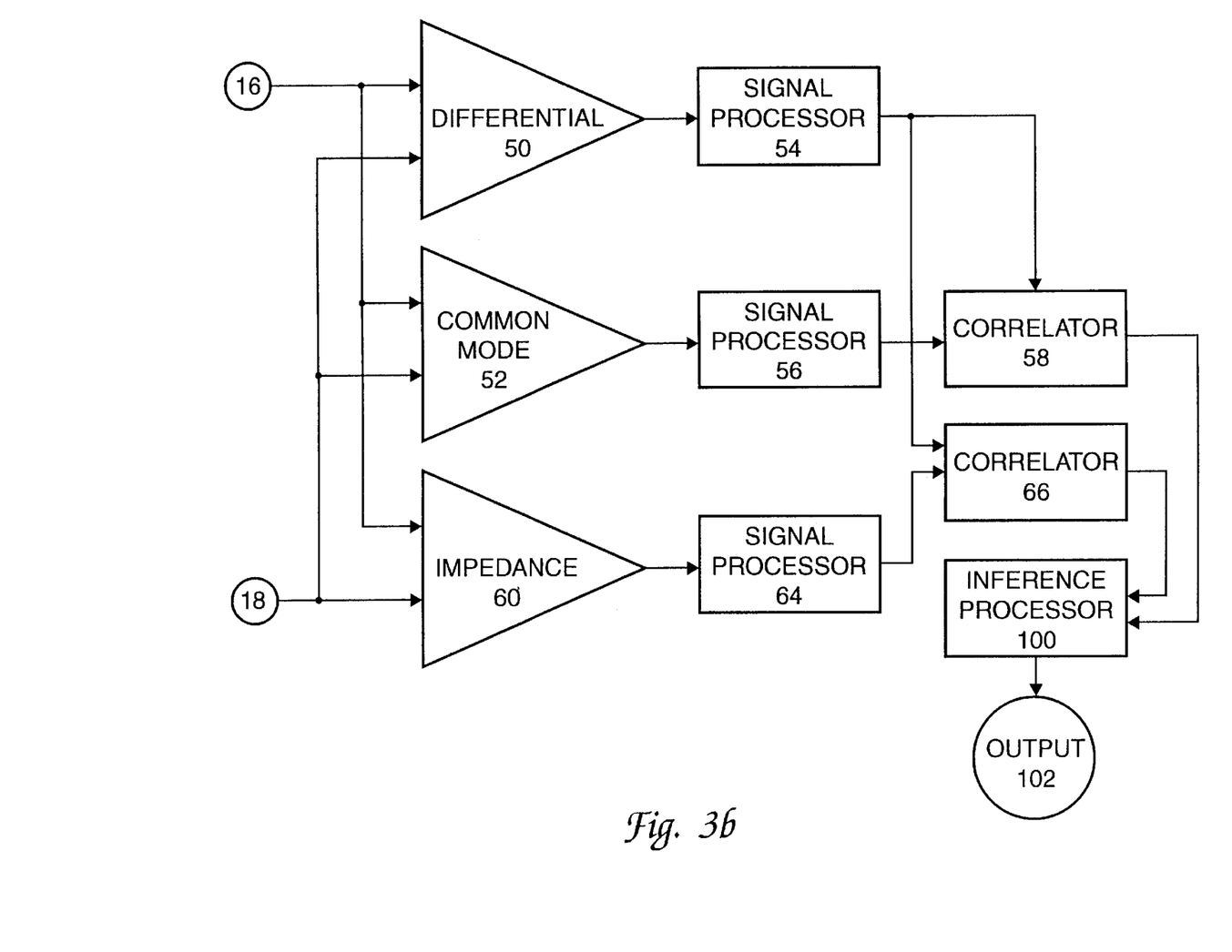
FIG. 3B is a simplified schematic diagram like that shown in FIG. 3A, wherein the input signal is also connected to an impedance detector. The detected impedance signal is also processed and provided to a correlator and inference processor.

FIG. 3B is a simplified circuit depicting the signal processing method for detecting both common-mode current and transthoracic impedance for use as artifact reference signals, which expands on the circuit shown in FIG. 3A. Again, the input signal is received across the electrodes 16, 18 and transmitted to differential-mode amplifier 50, and common-mode amplifier 52 which amplify the signal prior to transmitting the signal to the signals processors. The resulting signals are then transmitted to their respective signal processors 54, 56 which process the signals to emphasize particular features. The resulting processed signals are then transmitted to a correlator 58 which correlates the signals. Additionally the input signal is transmitted to impedance detector 60. Impedance detector 60 provides a transelectrode impedance signal to the signal processor 64. Signal processor 64 processes the signal from the impedance detector 60 to emphasize particular features of the signal. The resulting processed signal is then transmitted to a correlator 66 which correlates the signal 64 with the processed signal from the differential amplifier 54. Once the signals have been correlated at their respective correlators 58, 66, the resulting signals are transmitted to the inference processor 100 which then further evaluates the results of the correlators 58, 66 to provide an indication of the degree of corruption of the event signal of interest. The inference processor 100 provides an output 102 which may be further analyzed as discussed with respect to FIG. 4 below.

Figure 3C:
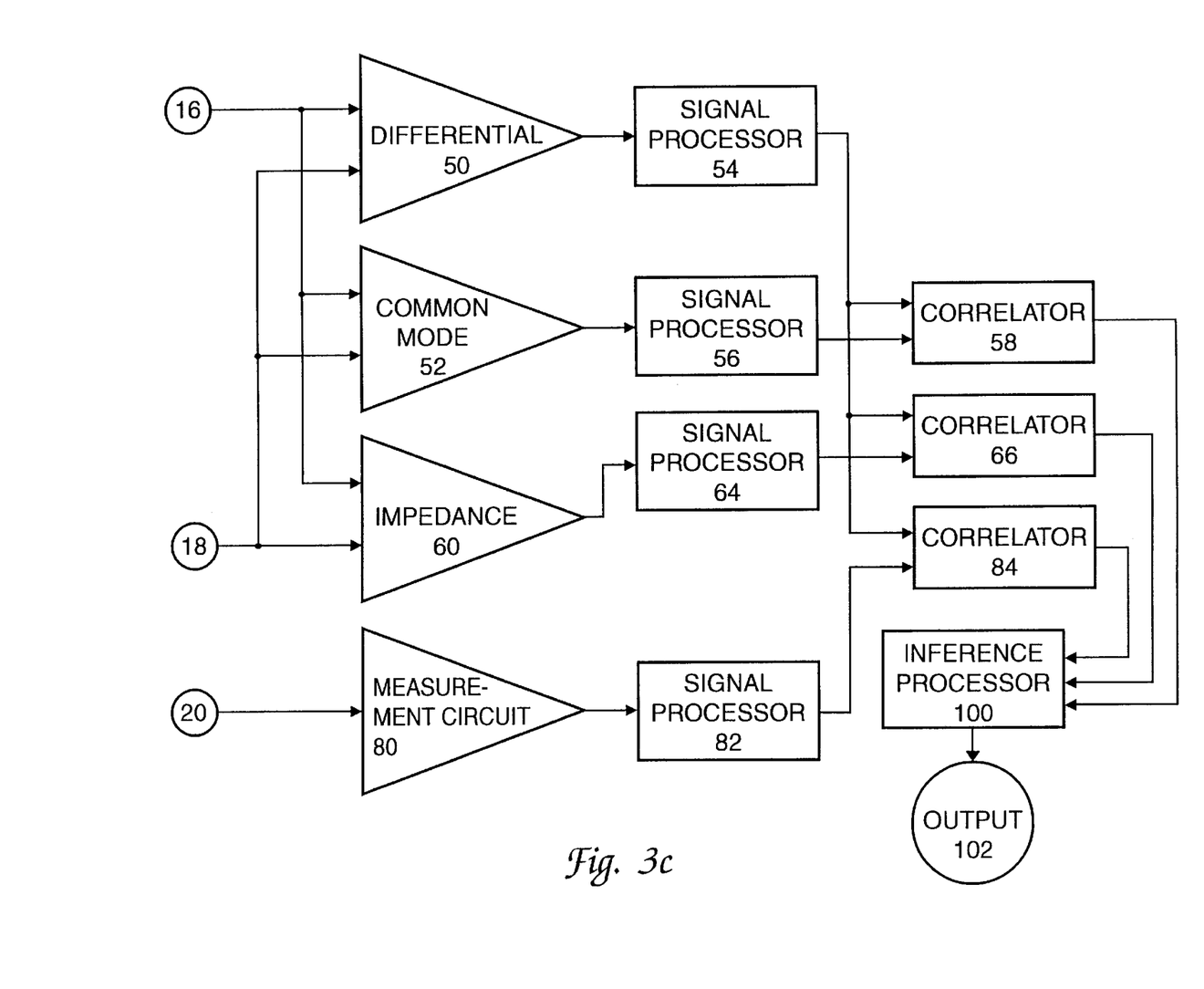
FIG. 3C is a simplified schematic diagram like that shown in FIG. 3B, wherein an additional sensor, such as a motion detector, is also measured, processed, and provided to a correlator and inference processor.

FIG. 3C is a simplified circuit similar to that shown in FIG. 3B, except that an additional sensor 20 is provided for detecting motion, for use as an additional independent non-event signal. The motion sensor 20 sends the signal to a motion measurement circuit 80 which detects the level of motion present. Thereafter the signal is sent to a signal processor 82 and provided to a correlator 84, where it is correlated with the processed signal from the differential amplifier 54. The correlated signal is then transmitted to the inference processor 100 where it is processed along with the correlated signals obtained as described with respect to FIG. 3B. The inference processor 100, then evaluates the signals to produce an output 102.

Figure 4A:
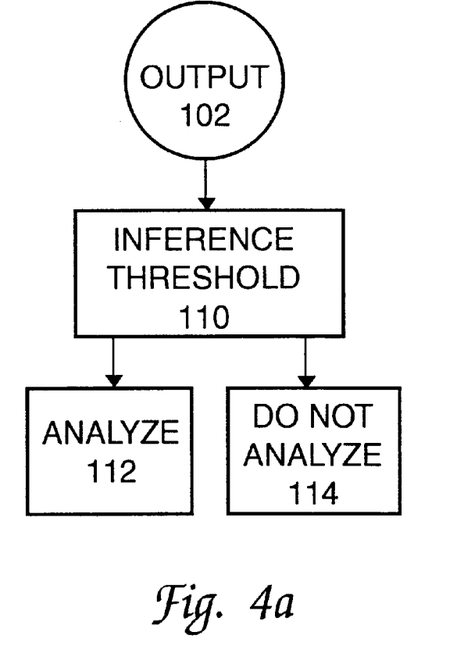
Figure 4B:
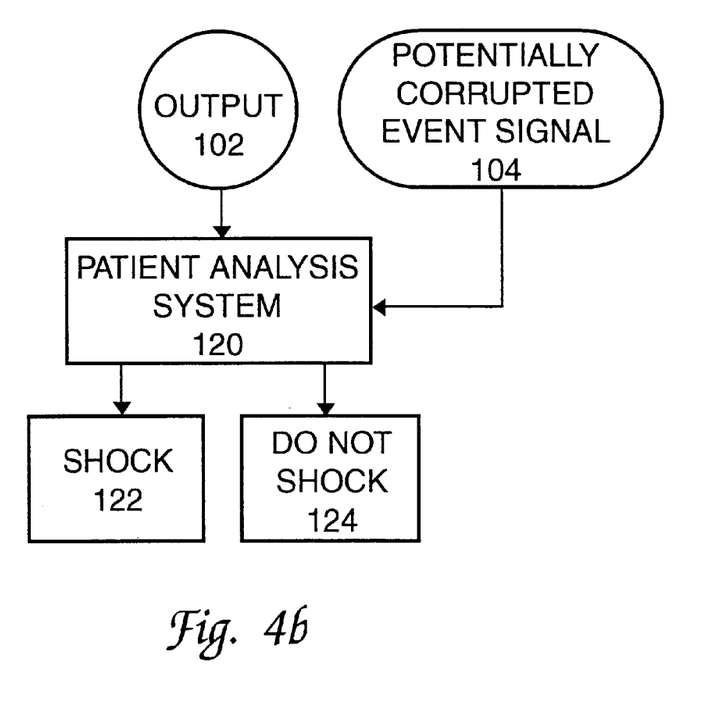
In FIG. 4B, the output is provided to an assessment system, such as a patient analysis system, and used in conjunction with the potentially corrupted event signal 104 to arrive at a more reliable treatment recommendation.

FIGS. 4A and 4B are block diagrams that show two alternative ways of processing the inference output 102 from FIGS. 3A through 3C. As shown in FIG. 4A, the output is compared to an inference threshold 110. If the output does not exceed the threshold, then the device proceeds to analyze 112 the potentially corrupted event signal (provided by differential amplifier 50). If the output exceeds the threshold, then the device does not analyze the signal 114. Thus the inference threshold 110 acts as a YES/NO decision maker with respect to processing the event signal.

As shown in FIG. 4B, the output is provided to a patient analysis system 120. The patient analysis system 120 provides a more robust analysis of the patient rhythm (provided by differential amplifier 50), by incorporating the probability of artifact 102, thus allowing the device to make a shock 122 or no shock 124 decision.

Figure 5:
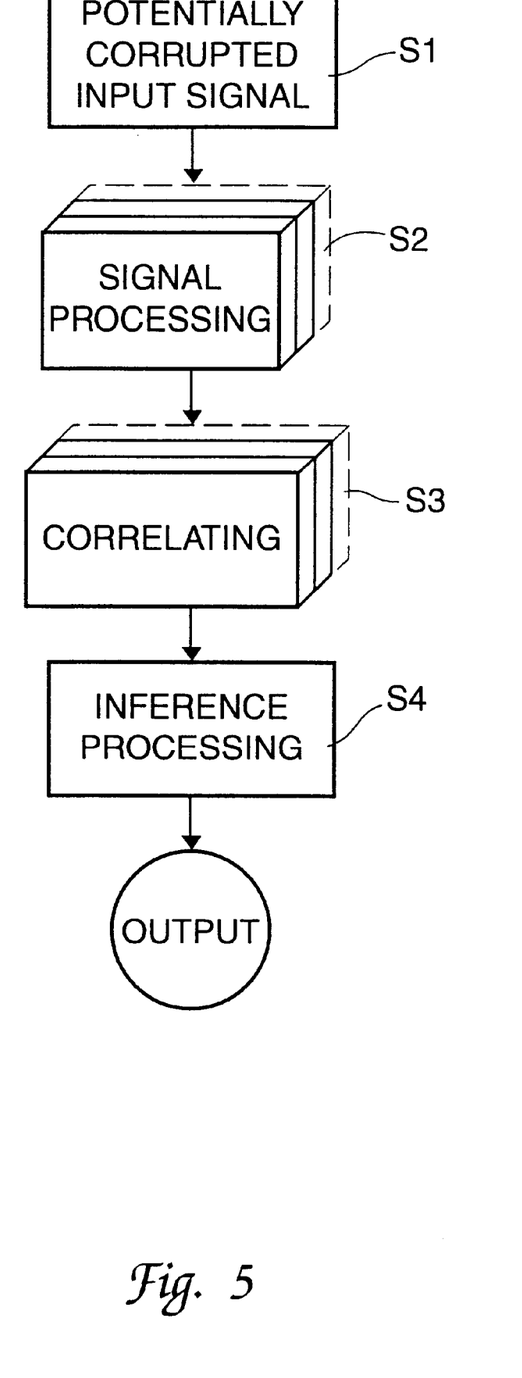
FIG. 5 is a flow chart demonstrating a method of the invention where one input signal comprising coexistent event and non-event signals is used.

FIG. 5 is a flow chart illustrating the processing steps associated with analyzing a patient input signal in order to determine whether to analyze the potentially corrupted cardiac event signal. According to step S1, an input signal comprises a potentially corrupted event signal combined with non-event signals. One or more signal processing steps (such as those described above with respect to FIGS. 3A–3C) occurs at step S2 depending upon the implementation. The signal processing is implemented in order to emphasize a particular feature of the data in the input signal. Various implementations of processing, discussed above, include known techniques such as filters, Fourier transforms, wavelet transforms, and joint time-frequency spectrograms.

For example, the lower spectral portion of a Fourier transform of an ECG signal might be correlated with a similarly processed impedance signal in order to enhance the detection of artifact resulting from a defibrillator operator performing CPR on a patient being monitored.

According to another example, a small scale detail of a wavelet transform of an ECG signal might be correlated with a similarly processed detail of a common-mode current to enhance detection of artifact resulting from electrostatic discharges. Such discharges can occur particularly in dry climates where an individual comes into close proximity with the defibrillator during monitoring of a patient.

The comparing/correlating step S3 performs the function of measuring similarities between the processed cardiac event signal and the processed non-event signals. Again, specific implementations of the comparison/correlation step were discussed above.

The resulting comparisons are then analyzed together by inference processing in step S4 in order to determine an indication of the degree of artifact present within the potentially corrupted cardiac event signal. The output of the inference processing step S4 may be used according to the block diagram of either FIG. 4A or FIG.4B, as discussed above.

As will be appreciated by those of skill in the art, the steps of FIG. 5 can be applied to situations where there is a single event signal or to situations where there are multiple event signals without departing from the scope of the invention.

While this invention has been described with respect to cardiac monitoring devices, it will be appreciated by those skilled in the art that the concepts may be applied to other types of measuring instruments, including, but not limited to, for example, seismographs.

As will be appreciated by those skilled in the art, many changes, modifications, variations and other uses and applications of the subject invention will, however, become apparent after considering this specification and the accompanying drawings which disclose preferred embodiments thereof. All such changes, modifications, variations and other uses and applications which do not depart from the spirit and scope of the invention are deemed to be covered by the invention, which is limited only by the claims which follow.

What is claimed:

1. An apparatus for detecting corruption of an event signal with artifact in an environment where the potentially corrupted event signal coexists with two or more non-event signals which may be related to the artifact, the apparatus comprising:

a sensor for providing an input signal, wherein the input signal comprises an event signal coexisting with two or more non-event signals;

a measurement system for receiving the input signal from the sensor and separating the received input signal into its constituent parts, wherein the measurement system comprises a receiver for receiving the input signal, a detector for detecting the event signal from the received input signal, and detectors for detecting the non-event signals from the received input signal;

correlators for comparing the detected event signal with each of the detected non-event signals to produce respective correlation signals; and an inference processor for analyzing the correlation signals to produce an indication of signal corruption.

2. The apparatus of claim 1 wherein the inference processor analyzes the correlation signals to determine if the event signal is corrupted.

3. The apparatus of claim 1 wherein the inference processor analyzes the correlation signals to determine a degree of corruption of the event signal.

4. The apparatus of claim 1 wherein the inference processor is selected from the group consisting of: peak detectors, polynomial regressions, fuzzy set operations, neural networks, probability estimators, and statistical classifiers.

5. The apparatus of claim 1 wherein the coexistent signals are selected from the group consisting of: differential voltage, impedance, and common-mode current.

6. The apparatus of claim 1 wherein the apparatus has a plurality of signal processors for processing the event and non-event signals prior to correlation.

7. The apparatus of claim 6 wherein the signal processors are selected from the group consisting of linear and non-linear transforms.

8. The apparatus of claim 7 wherein the signal processors are selected from the group consisting of: filters, Fourier transforms, wavelet transforms, and joint time-frequency spectrograms.

9. An apparatus for detecting corruption of an event signal with artifact in an environment where the potentially corrupted event signal and non-event signals which may be related to the artifact exist independently, the apparatus comprising:

a sensor for providing a first input signal, wherein the first input signal comprises the event signal;

a plurality of additional sensors for providing a plurality of additional input signals, wherein the additional input signals comprise non-event signals;

a measurement system for receiving the input signals from the sensors and detecting the event and non-event signals, wherein the measurement system comprises a receiver for receiving the first input signal, a detector for detecting an event signal from the received first input signal, receivers for receiving the additional input signals, and detectors for detecting the non-event signals from the received additional input signals;

correlators for comparing the detected event signal with each of the detected non-event signals to produce respective correlation signals; and an inference processor for analyzing the correlation signals to produce an indication of signal corruption.

10. The apparatus of claim 9 wherein the inference processor analyzes the correlation signals to determine if the event signal is corrupted.

11. The apparatus of claim 9 wherein the inference processor analyzes the correlation signals to determine a degree of corruption of the event signal.

12. The apparatus of claim 9 wherein the inference processor is selected from the group consisting of: peak detectors, polynomial regressions, fuzzy set operations, neural networks, probability estimators, and statistical classifiers.

13. The apparatus of claim 9 wherein the apparatus has a plurality of signal processors for processing the event and non-event signals prior to correlation.

14. The apparatus of claim 13 wherein the signal processors are selected from the group consisting of linear and non-linear transforms.

15. The apparatus of claim 13 wherein the signal processors are selected from the group consisting of: filters, Fourier transforms, wavelet transforms, and joint time-frequency spectrograms.

16. The apparatus of claim 9 in an environment where the input signals may have additional coexistent non-event signals, wherein the measurement system additionally separates the input signals from the sensors into their constituent parts providing additional non-event signals.

17. In an apparatus for detecting corruption of an event signal with artifact in an environment where the potentially corrupted event signal coexists with two or more non-event signals which may be related to the artifact, a method for determining the integrity of the event signal comprising:

(a) sensing an input signal;

(b) detecting the input signal by a measurement system;

(c) separating the input signal into constituent parts, comprising an event signal and two or more non-event signals;

(d) correlating the resulting event signal with each of the resulting non-event signals to produce respective correlation signals;

(e) providing the correlation signals to an inference processor; and (f) determining whether the event signal can be used with confidence.

18. The method of claim 17 wherein the inference processor examines the correlation signals to determine if the event signal is corrupted.

19. The method of claim 17 wherein the inference processor analyzes the correlation signals to determine a degree of corruption of the event signal.

20. The method of claim 17 wherein step (b) is repeated a plurality of times to provide more than one input to the device.

21. In an apparatus for detecting corruption of an event signal with artifact in an environment where the potentially corrupted event signal and non-event signals which may be related to the artifact exist independently, a method for determining the integrity of the event signal comprising:

(a) sensing a plurality of input signals with a plurality of sensors;

(b) detecting an event signal from one input signal;

(c) detecting a non-event signal from an additional input signal;

(d) correlating the resulting event signal with each non-event signal to produce respective correlation signals;

(e) providing the correlation signals to an inference processor;

(f) determining whether the event signal can be used with confidence; and (g) repeating step (c) a plurality of times to provide more than one non-event signal to the device.

22. The method of claim 21 wherein a detected input signal is further separated into its constituent parts to provide additional non-event signals to the device.

23. The method of claim 21 wherein the inference processor examines the correlation signals to determine if the event signal is corrupted.

24. The method of claim 21 wherein the inference processor analyzes the correlation signals to determine a degree of corruption of the event signal.

* * * * *